United States Patent [19]

Harvey, Sr. et al.

[11] Patent Number: 4,609,355
[45] Date of Patent: Sep. 2, 1986

[54] DENTAL PROSTHESIS AND METHOD

[76] Inventors: Arthur E. Harvey, Sr., Davis Ave., R.D. #2, Pawcatuck, Conn. 06379; Thomas J. Harvey, 64 Floral Park Blvd., Pawtucket, R.I. 02861

[21] Appl. No.: 751,371

[22] Filed: Jul. 2, 1985

[51] Int. Cl.⁴ .............................................. A61C 13/22
[52] U.S. Cl. ..................................... 433/181; 433/177
[58] Field of Search .............. 433/172, 177, 181, 182, 433/180

[56] References Cited

U.S. PATENT DOCUMENTS

| | | | |
|---|---|---|---|
| 3,717,931 | 2/1973 | Konig | 433/177 |
| 4,163,318 | 8/1979 | Tigani | 433/172 |
| 4,348,181 | 9/1982 | Dawson | 433/172 |

Primary Examiner—Robert Peshock
Attorney, Agent, or Firm—Salter & Michaelson

[57] ABSTRACT

A permanent dental prosthesis and a method of installing the prosthesis in the mouth of a patient to replace a missing tooth. The prosthesis comprises a body portion, first and second lugs which project outwardly from opposite side edges of the body portion and which are inwardly slidable with respect to each other, a spring element for biasing the lugs apart and a cap receivable on the body portion for defining an outer tooth-like configuration for the prosthesis. In accordance with the method, the prosthesis is installed between a pair of spaced teeth by first forming elongated notches in the inwardly facing edges of the teeth and then assembling and cementing the prosthesis between the teeth so that the lugs are received and cemented in the notches. The spring element is preferably then removed, and a cap is formed over the body portion to provide an outer configuration for the prosthesis which simulates a natural tooth.

11 Claims, 6 Drawing Figures

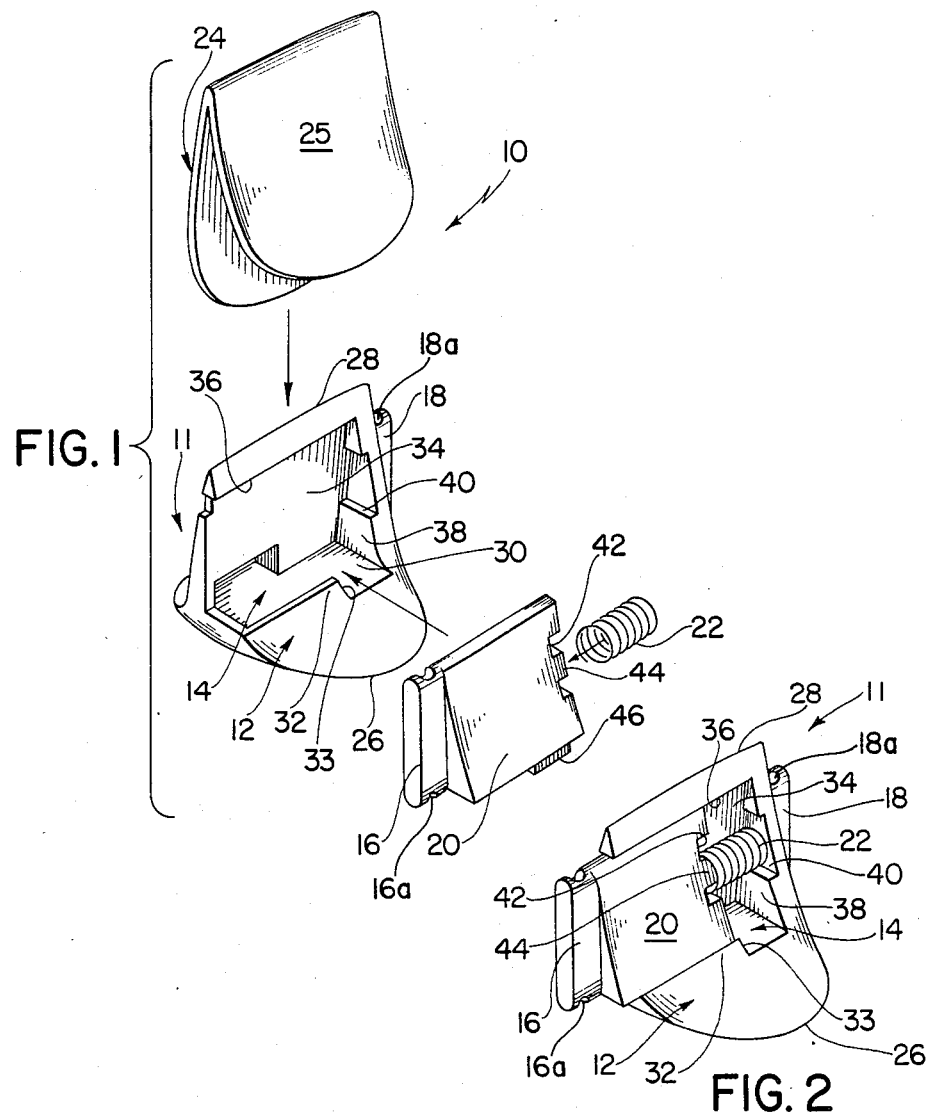
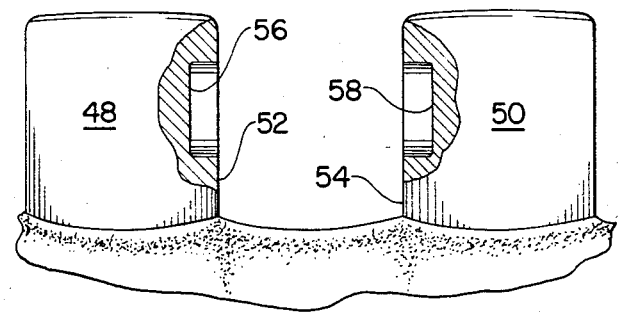

DENTAL PROSTHESIS AND METHOD

BACKGROUND AND SUMMARY OF THE INVENTION

The instant invention relates to the field of dentistry and more particularly to a permanent dental prosthesis and to a method of installing the prosthesis in the mouth of a patient.

A variety of different types of dental prostheses have been heretofore available for replacing missing teeth in the mouths of patients. Of these, possibly the most common type of dental prosthesis heretofore available has been the conventional dental bridge which can be utilized for removably replacing one or more teeth. However, it has been found that in many cases it is desirable, for both functional and aesthetic reasons, for a dental prosthesis to be permanently securable in the mouth of a patient to provide a permanent replacement for a missing tooth. The devices disclosed in the U.S. Pats. Nos. to MILLER, No. 1,685,289; STOLOFF, No. 1,702,282; KONIG, No. 3,717,931; TIGANI, No. 4,163,318; YOON, No. 4,302,187; ROMAGNOLI, No. 4,345,901; DAWSON, No. 4,348,181; WEISSMAN, No. 4,380,434; and YOON, No. 4,406,622, which represent the closest prior art to the instant invention of which the applicant is aware, are exemplary of a variety of different types of dental prosthesis constructions, some of which are adapted for permanent installations. However, these references are believed to be of only general interest with respect to the prosthesis of the instant invention since they fail to suggest an effective permanent dental prosthesis which embodies the structural features of the prosthesis of the instant invention, which is practical for a wide variety of applications, and which is adapted to be simply and easily installed in the mouth of a patient. They are also felt to be of only general interest with respect to the method of the instant invention since they fail to suggest a method of installing a prosthesis which includes the inventive method steps herein set forth.

The instant invention provides an effective dental prosthesis and method which can be utilized for permanently replacing missing teeth in the mouths of patients. The prosthesis of the instant invention comprises a body portion dimensioned to be received between two spaced teeth in the mouth of a patient, first and second inwardly slidable lug means projecting outwardly from opposite side edges of the body portion, means resiliently biasing the lug means outwardly with respect to each other, and cap means receivable on the body portion for defining a tooth-like outer configuration of the prosthesis. For use of the prosthesis, inwardly facing notches are formed in the inwardly facing side edges of a pair of spaced teeth and the prosthesis is installed and assembled in the space between the teeth so that the lug means are received and cemented in the notches to secure the prosthesis in position. In the preferred embodiment of the prosthesis, the body portion has a laterally extending channel formed therein which is open along one side edge of the body portion and closed along the other side edge thereof, and the prosthesis further comprises a slide member which is slidably received in the channel. Further in the preferred embodiment, the first lug means is formed on an end of the slide member, the second lug means is integrally formed with the body portion adjacent the closed end of the channel, and the biasing means engages the slide member and the body portion to urge the first and second lug means outwardly with respect to each other. Also in the preferred embodiment, the biasing means is removable from the prosthesis so that it can be removed during the installation of the prosthesis in the mouth of a patient.

The method of the instant invention comprises the steps of forming notches in the inwardly facing side edges of a pair of spaced teeth so that the notches are dimensioned to receive the lug means of the prosthesis therein, assembling the prosthesis between the teeth so that the lug means are received in the notches, cementing the lug means in their respective notches, allowing the cement to cure, and assembling the cap portion on the body portion. In the preferred form of the method, the side edges of the adjacent teeth are ground to provide substantially flat, parallel inwardly facing side edge surfaces thereon before the notches are formed in the teeth. Further in the preferred form of the method, the cementing step is carried out by applying cement to the notches before the prosthesis is assembled between the teeth, and after the cement has cured, any remaining open areas in the notches are filled with a dental composite material. Still further in the preferred method, after the curing step has been completed, the biasing means is permanently removed from the prosthesis before the cap means is assembled thereon and the step of applying the cap means includes the steps of applying a dental ceramic composite material over the body portion and the slide member to fill any void areas therein after the biasing means has been removed and thereafter applying a preformed acrylic or porcelain veneer over the ceramic composite material to define an outer tooth-like configuration for the prosthesis.

As a result of the above features the prosthesis and method of the instant invention can be effectively utilized for permanently replacing one or more missing teeth in the mouth of a patient. The prosthesis can normally be easily assembled and installed in the mouth of a patient by a dentist without requiring custom dental lab work. The biasing means of the prosthesis urges the lug means outwardly so that the lug means are snapped into position in their respective notches as soon as the prosthesis has been placed in position, and after the lug means have been cemented in their respective notches, the biasing means is removed from the prosthesis and a ceramic composite material is applied to the body and to the slide member before the acrylic veneer is assembled thereon. Further, the prosthesis can be effectively constructed in different configurations and dimensions for replacing teeth in various different areas of the mouths of patients or for replacing several teeth. Accordingly, the prosthesis can be effectively utilized for providing a firm, solid, durable and securely held replacement for one or more teeth in the mouth of a patient. Further, because of the overall simplicity of the prosthesis, it can normally be permanently installed in the mouth of a patient by a dentist in a short period of time, and custom dental work is not normally required to prepare the prosthesis for the patient.

Accordingly, it is a primary object of the instant invention to provide an effective permanent dental prosthesis.

Another object of the instant invention is to provide an effective method of installing a permanent dental prosthesis in the mouth of a patient.

An even further object of the instant invention is to provide a permanent dental prosthesis which can be assembled and installed in a dentist's office and which does not require custom dental lab work to adapt it for installation in the mouth of a patient.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is an enlarged exploded perspective view of the prosthesis of the instant invention;

FIG. 2 is an enlarged perspective view of the prosthesis without the cap portion thereof;

FIG. 3 is a front elevational view of a pair of spaced teeth which have been prepared to receive the prosthesis of the instant invention therebetween.

DESCRIPTION OF THE INVENTION

Figure 4:
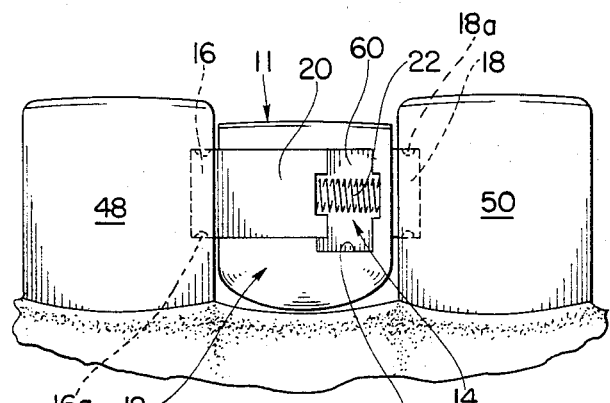
FIGS. 4–6 are sequential views illustrating the installation of the prosthesis between the pair of teeth.
Figure 5:
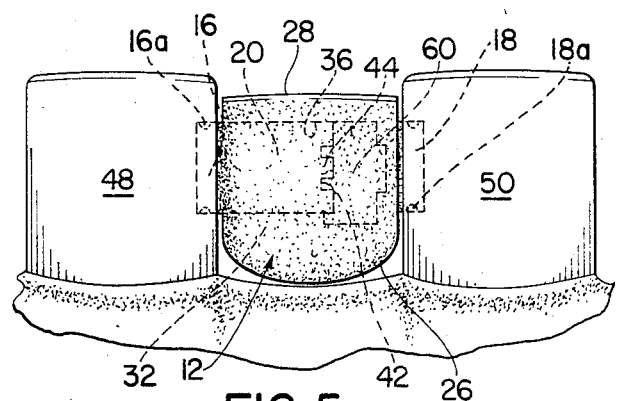
Figure 6:
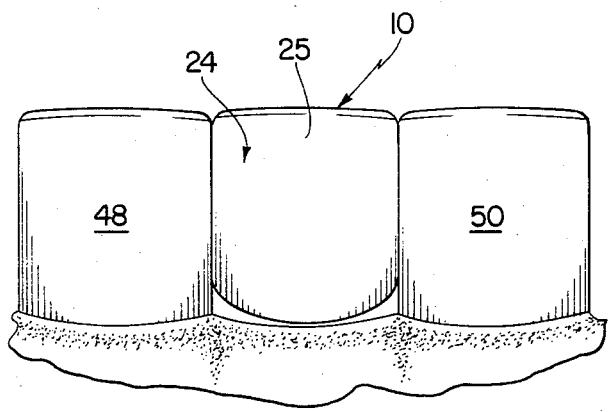

Referring now to the drawings, the prosthesis of the instant invention is illustrated in FIGS. 1 and 6 and generally indicated at 10. The prosthesis 10 comprises a subassembly generally indicated at 11 which comprises a body portion generally indicated at 12 having a channel 14 formed therein, first and second lug elements 16 and 18, respectively, having undercuts 16a and 18a, respectively, a slide member 20, and a spring element 22. In addition to the subassembly 11, the prosthesis 10 further comprises a cap member 24 comprising a premolded veneer 25 which is receivable on the subassembly 11 to define a tooth-like outer configuration for the prosthesis 10. The prosthesis 10 is adapted to be assembled in accordance with the method of the instant invention to provide a permanent dental prosthesis which is supported by a pair of adjacent teeth as will hereinafter be more fully set forth. It should be pointed out, however, that although the prosthesis 10 as herein set forth is adapted to replace a single tooth in the mouth of a patient, other embodiments of the prosthesis which are adapted to replace a plurality of teeth are also contemplated.

The body portion 12 is preferably made of a suitable corrosion resistant metal such as stainless steel, it is preferably formed in a configuration which is similar to that of a human tooth, such as the generally wedge-shaped configuration illustrated in FIG. 1 and FIG. 2, and it has a base end 26 which is preferably formed in a rounded or mushroom-shaped configuration (not shown) so that it is receivable adjacent the gum of a patient, and a tapered end 28. The channel 14, which is formed in the central portion of one side of the body portion 12, is defined by a bottom wall 30 having a raised peripheral rim 32 which extends around a portion thereof and defines an open slot 33 adjacent an end of the bottom wall 30, and a vertical wall 34 which extends from the bottom wall 30 to a laterally extending ridge 36 adjacent the end 28. One end of the channel 14 is defined by a closed vertical end wall 38 having a slot 40 therein, whereas the opposite end of the channel 14 is open. The second lug 18 is preferably integrally formed with the body portion 12 along the outwardly facing edge thereof which is adjacent the closed end of the channel 14.

The slide member 20 is also preferably made of a corrosion resistant metal such as stainless steel and it is dimensioned and configured to be received in the channel 14 in the body portion 12 so that it is laterally slidable therein and vertically retained by the bottom wall 30 and the ridge 36. The first lug 16 is preferably integrally formed at one end of the slide member 20 and the opposite end of the slide member 20 is formed with a pair of spaced grooves 42 therein which cooperate to define a center pin 44 for receiving the spring element 22. The slide member 20 is preferably formed so that when it is received in the channel 14, it cooperates with the body portion 12 for defining a generally tooth-like configuration of the subassembly 11, and it further includes a shoe 46 which rests on the bottom wall 30 of the channel 14 for slidably supporting the slide member 20 thereon in the subassembly 11. In this regard, the slot 33 is dimensioned to receive the shoe 46 therethrough during the assembly of the subassembly 11 and thereafter the spring 22 biases the slide member 20 to a position wherein the shoe 46 engages the rim 32 in order to retain the slide member 20 in the channel 14 so that the first lug 16 projects outwardly from the edge of the body portion 12 adjacent the open end of the channel 14.

The spring element 22 preferably comprises a coil spring which is also preferably made of a corrosion resistant material and it is received on the pin 44 and in the slot 40 for biasing the slide member 20 toward the open end of the channel 14. Accordingly, the lugs 16 and 18 which extend outwardly from opposite side edges of the body portion 12 are biased outwardly and away from each other by the spring element 22, although they are inwardly slidable against the force of the spring element 22. The spring element 22 is, however, preferably removably received in the subassembly 11 so that it can be removed before the cap member 24 is installed thereon.

The cap member 24 preferably comprises the premolded veneer 25 and a conventional dental composite material (not shown). The veneer 25 is preferably formed with a tooth-like outer configuration and it is preferably colored to match the adjacent natural teeth in the patient's mouth. The veneer 25 is further dimensioned and configured to be received over the subassembly 11 and it is preferably made of a suitable dental porcelain or acrylic material. The dental composite material preferably comprises either a conventional dental composite resin or ceramic composite, such as P-10 (3M TM) and it is applied in a moldable state over the subassembly 11 during the assembly of the prosthesis 10 in the mouth of a patient. Specifically, the composite material is applied in order to provide an adhesive base for the veneer 25 and in order to fill any voids which are present in the subassembly 11 so that the completed prosthesis 10 has a substantially solid construction. Further in this regard, however, it should be pointed out that it is also possible to form the cap member 24 entirely from the composite material, and therefore other embodiments of the prosthesis of the instant invention which do not include a preformed veneer 25 are contemplated.

While it is seen that the prosthesis of the instant invention provides an effective means for permanently replacing one or more teeth in the mouth of a patient, it will be apparent that the specific prosthesis which is utilized for a particular application should be selected and adapted to meet the specific requirements of the application with regard to the dimensions, configuration, and color of the prosthesis. Further in this regard, the lugs 16 and 18 are also preferably configured and dimensioned to support the prosthesis in a manner which resists the forces, including twisting forces, to which it is normally exposed in the particular area of the mouth where it is mounted.

The sequential steps required for the installation of the prosthesis 10 in the mouth of a patient are illustrated in FIGS. 3-6. In this regard, however, although the method herein illustrated and described relates to the installation of the prosthesis 10 which is adapted for replacing a single tooth in the mouth of a patient, it will be understood that the method of the instant invention is also applicable for installing other similar prostheses which are adapted to replace multiple teeth in corresponding openings in the mouths of patients. In any event, as illustrated in FIG. 3, in order to install the prosthesis 10 between a pair of spaced teeth 48 and 50, the opposed inwardly facing side edges of the teeth 48 and 50 are preferably first ground to provide substantially flat inwardly facing substantially parallel side edge surfaces 52 and 54 thereon to adapt the teeth 48 and 50 to receive the prosthesis 10 therebetween and thereafter elongated notches 56 and 58 are formed in the inwardly facing side edge surfaces 52 and 54 of the teeth 48 and 50, respectively. In this regard, the notches 56 and 58 are preferably formed so that they are dimensioned and configured to snugly receive the lugs 16 and 18 therein in order to firmly position the prosthesis 10 in the desired orientation in the mouth of the patient, and preferably the interior surfaces of the notches 56 and 58 are acid etched in order to increase their receptivity to dental cements which are utilized for securing the prosthesis 10 in the mouth. In any event, after the notches 56 and 58 have been fully formed, the subassembly 11 is installed in the mouth of the patient so that the lugs 16 and 18 are snap-received in their respective notches 56 and 58 as a result of the spring element 22 and a dental cement is applied to the lugs 16 and 18 to secure them in their respective notches 56 and 58. In this regard, preferably the lugs 16 and 18 are cemented in their respective notches by applying a suitable dental cement to the surfaces of the notches 56 and 58 before the subassembly 11 is installed between the teeth 48 and 50 to ensure that all of the surfaces of the notches 56 and 58 are bonded to the adjacent surfaces of their respective lugs 16 and 18. Further, a sufficient amount of cement is applied to the lugs 16 and 18 so that the undercuts 16a and 18a enhance the firm retention of the subassembly 11 between the teeth 48 and 50. In any case, after the subassembly 11 has been assembled between the teeth 48 and 50 and the cement has been applied, the cement is allowed to cure and a dental composite material of the type hereinabove described is thereafter applied to any void areas remaining in the notches 56 and 58. In the preferred form of the method, the spring 22 is then removed from the subassembly 11 and the ceramic composite material is applied over the remaining components of the subassembly 11 in order to fill any void areas therein, such as the area 60 illustrated in FIGS. 4 and 5 which is defined by that portion of the channel 14 not occupied by the slide member 20. Further amounts of ceramic composite material are also preferably applied over the exposed portions of the lugs 16 and 18 and over the surfaces of the base portion 12 and the slide member 20 in order to provide a firm foundation for the veneer 25. After the ceramic composite material has been applied in this manner, the veneer 25 is preferably assembled over the composite material on the base portion 12 and the slide member 20 to provide an outer casing for the prosthesis 10 and to define an outer configuration thereof which simulates a natural tooth as illustrated in FIG. 6. It should be pointed out, however, that other forms of the method of the instant invention which do not include the installation of the veneers, but wherein caps or casings are formed entirely from dental composite materials are contemplated. In any event, after the prosthesis 10 has been fully assembled and installed in the mouth of the patient and the cements and composite materials have cured, excess amounts of these materials are removed from the prosthesis 10, and the adjacent teeth 48 and 50, and the prosthesis 10 may be polished to whatever extent is necessary.

It is seen therefore that the instant invention provides an effective dental prosthesis and method for installing the prosthesis in the mouth of a patient. The prosthesis 10 can be effectively supported in the mouth of a patient by the adjacent teeth 48 and 50 and it can be permanently installed in accordance with the method to provide an effective and durable prosthesis. The outwardly biased lugs 16 and 18 of the prosthesis make it simple and easy to install the prosthesis in the mouth of a patient so that it can be effectively installed in a patient in a dentist's office. Accordingly, for these reasons as well as the other reasons herein set forth, it is seen that the prosthesis and method of the instant invention represent significant advancements in the dental art, which have substantial merit from both medical and commercial standpoints.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A dental prosthesis comprising:
   a. a substructure comprising;
      i. a body portion dimensioned to be received between two spaced teeth in the mouth of a patient, said body portion having an open laterally extending channel formed therein which is open at one end thereof along one side edge of said body portion;
      ii. a slide member received in said channel so that it is longitudinally slidable therein;
      iii. first lug means on an end of said slide member and receivable in a notch in the inwardly facing side edge of one of said teeth;
      iv. said slide member being dimensioned and being positioned in said channel so that said first lug means projects outwardly from said one side edge of said body portion, and so that a void area is defined in said channel adjacent the end of said slide member opposite from said first lug means;
      v. second lug means projecting outwardly from the other side edge of said body portion and receivable in a notch in the inwardly facing side edge of the other of said teeth; and
      vi. means biasing said first and second lug means apart;

b. a hardening dental composite material receivable in said void area for permanently securing said slide member with respect to said body portion and said first and second lug means with respect to each other; and c. cap means receivable on said substructure and said composite material for defining an outer configuration of said prosthesis which simulates a natural tooth.

2. In the prosthesis of claim 1, said second lug means being immovable with respect to said body.

3. In the prosthesis of claim 1, said second lug means being integrally formed with said body.

4. In the prosthesis of claim 1, said biasing means being removable.

5. In the prosthesis of claim 1, said channel being open at one end thereof and closed at the opposite end thereof, said first lug means projecting outwardly from the open end of said channel, said second lug means being formed on said body portion adjacent the closed end of said channel.

6. In the prosthesis of claim 5, said biasing means being interposed between said slide member and the closed end of said channel.

7. A method of installing a dental prosthesis between two spaced teeth wherein the prosthesis includes a substructure comprising a body portion dimensioned to be received between said teeth and having an open laterally extending channel therein which is open at one end thereof along one side edge of said body portion, a slide member in said channel, a first lug on an end of said slide member, said slide member being dimensioned and positioned in said channel so that said first lug projects outwardly from said one side edge of said body portion and so that a void area is defined in said channel adjacent the end of said slide member opposite from said first lug, a second lug projecting outwardly from the other side edge of said body portion, means biasing said first and second lugs apart, said method comprising the steps of:

a. forming notches in the inwardly facing side edges of said teeth, said notches being dimensioned to receive said lugs therein;

b. assembling said substructure between said teeth so that said lugs are received in said notches;

c. cementing said lugs in said notches;

d. allowing said cement to cure;

e. filling said void area with a hardening dental composite material to secure said slide member with respect to said body portion and said first and second lugs with respect to each other; and f. applying a cap portion on said substructure and said composite material for defining an outer configuration of said prosthesis which simulates a natural tooth.

8. The method of claim 1 further comprising the step of grinding said teeth to form substantially flat, parallel inwardly facing side edge surfaces thereon before forming said notches in said teeth, said notches being formed in said side edge surfaces.

9. In the method of claim 8, said cementing step comprising applying cement to said notches before assembling said prosthesis between said teeth.

10. The method of claim 8 further comprising the step of filling said notches around said lugs with a dental compound after said curing step.

11. The article formed by the method of claim 8.

* * * * *